United States Patent [19]
Hunter et al.

[11] Patent Number: 6,077,255
[45] Date of Patent: *Jun. 20, 2000

[54] ABSORBENT ARTICLES HAVING UNDERGARMENT COVERING COMPONENTS WITH MECHANICAL FASTENERS HAVING IMPROVED TACTILE PROPERTIES

[75] Inventors: Allison Kay Hunter, West Chester; Nicholas Albert Ahr, Cincinnati, both of Ohio; Bruce William Lavash, Bad Homburg, Germany

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/869,867

[22] Filed: Jun. 2, 1997

Related U.S. Application Data

[63] Continuation of application No. 08/503,348, Jul. 17, 1995, Pat. No. 5,676,652.

[51] Int. Cl.[7] .............................. A61F 13/15; A61F 13/20
[52] U.S. Cl. ............................................ 604/387; 604/391
[58] Field of Search .................................... 604/373, 385, 604/387, 391

[56] References Cited

U.S. PATENT DOCUMENTS

| | | |
|---|---|---|
| 2,787,271 | 4/1957 | Clark . |
| 3,397,697 | 8/1968 | Richard . |
| 3,885,255 | 6/1975 | Shah et al. . |
| 4,166,464 | 9/1979 | Korpman . |
| 4,285,343 | 8/1981 | McNair . |
| 4,536,433 | 8/1985 | Sagi et al. . |
| 4,553,550 | 11/1985 | Hattori . |
| 4,589,876 | 5/1986 | Van Tilburg . |
| 4,608,047 | 8/1986 | Mattingly . |
| 4,687,478 | 8/1987 | Van Tilburg . |
| 4,834,739 | 5/1989 | Linker, III et al. . |
| 4,900,320 | 2/1990 | McCoy . |
| 4,911,701 | 3/1990 | Mavinkurvue . |
| 4,917,697 | 4/1990 | Osborn et al. . |
| 4,940,462 | 7/1990 | Salerno . |
| 4,950,264 | 8/1990 | Osborn . |
| 5,007,906 | 4/1991 | Osborn, et al. . |

(List continued on next page.)

FOREIGN PATENT DOCUMENTS

| | | |
|---|---|---|
| 0 426 235 A2 | 5/1991 | European Pat. Off. . |
| 0 446 818 A2 | 9/1991 | European Pat. Off. . |
| 0 467 184 A1 | 1/1992 | European Pat. Off. . |
| 0 511 905 A1 | 1/1992 | European Pat. Off. . |
| 0 539 032 A1 | 4/1993 | European Pat. Off. . |
| 0 590 675 | 4/1994 | European Pat. Off. . |
| 40-36391 | 12/1965 | Japan . |
| 236101 | 10/1993 | New Zealand . |
| 2 168 253 | 6/1986 | United Kingdom . |
| WO 92/07535 | 5/1992 | WIPO . |
| WO 93/01785 | 2/1993 | WIPO . |
| WO 93/01786 | 2/1993 | WIPO . |
| WO 93/06805 | 4/1993 | WIPO . |
| WO 93/23610 | 10/1994 | WIPO . |
| WO 95/03025 | 2/1995 | WIPO . |

Primary Examiner—Mark O. Polutta
Attorney, Agent, or Firm—Jeffrey V. Bamber

[57] ABSTRACT

Absorbent articles such as sanitary napkins, panty liners, and incontinence pads that are provided with mechanical fasteners are disclosed. Preferred embodiments have undergarment covering components (or "side wrapping elements") that automatically fold along the sides of a wearer's panties and provide an alternative to conventional side flaps. The side wrapping elements of such embodiments have at least one zone of extensibility and at a region therein that is stiffer than the zone of extensibility. The side wrapping elements are provided with mechanical fasteners in the form of hair-like projections that have improved tactile properties.

11 Claims, 4 Drawing Sheets

U.S. PATENT DOCUMENTS

| | | |
|---|---|---|
| 5,009,653 | 4/1991 | Osborn . |
| 5,011,480 | 4/1991 | Gossens et al. . |
| 5,125,918 | 6/1992 | Seidy . |
| 5,180,534 | 1/1993 | Thomas, et al. . |
| 5,281,209 | 1/1994 | Osborn, et al. . |
| 5,300,058 | 4/1994 | Goulait, et al. . |
| 5,315,740 | 5/1994 | Provost . |
| 5,324,278 | 7/1994 | Visscher, et al. . |
| 5,344,416 | 9/1994 | Niihara . |
| 5,346,486 | 9/1994 | Osborn, et al. . |
| 5,389,094 | 2/1995 | Lavash, et al. . |
| 5,392,498 | 2/1995 | Goulait et al. . |
| 5,558,663 | 9/1996 | Weinberger, et al. . |
| 5,584,829 | 12/1996 | Lavash, et al. . |
| 5,611,790 | 3/1997 | Osborn, et al. . |
| 5,676,652 | 10/1997 | Hunter et al. .......................... 604/391 |

ABSORBENT ARTICLES HAVING UNDERGARMENT COVERING COMPONENTS WITH MECHANICAL FASTENERS HAVING IMPROVED TACTILE PROPERTIES

This is a continuation of U.S. patent application Ser. No. 08/503,348, filed Jul. 17, 1995 (now U.S. Pat. No. 5,676, 652).

FIELD OF THE INVENTION

The present invention relates to absorbent articles such as sanitary napkins, panty liners, and incontinence pads. More particularly, the present invention relates to sanitary napkins that have undergarment covering components (or "side wrapping elements") that are provided with mechanical fasteners. Still more particularly, the present invention relates to sanitary napkins having side wrapping elements that automatically fold or wrap the sides of a wearer's undergarments when the undergarments are pulled up, providing an alternative to conventional side flaps which have mechanical fasteners with improved tactile properties.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body. Sanitary napkins both with and without side flaps (or wings) are disclosed in the literature and are available in the marketplace.

Generally when sanitary napkins are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are particularly effective for preventing exudates from soiling the edges of the wearer's panties.

Sanitary napkins having flaps of various types are disclosed in U.S. Pat. No. 5,267,992, entitled "Shaped Sanitary Napkin With Flaps", which issued Dec. 7, 1993; U.S. Pat. No. 4,687,478, entitled "Shaped Sanitary Napkin With Flaps", which issued to Van Tilburg on Aug. 18, 1987; U.S. Pat. No. 4,608,047, entitled "Sanitary Napkin Attachment Means", which issued to Mattingly on Aug. 26, 1986; U.S. Pat. No. 4,589,876, entitled "Sanitary Napkin", which issued to Van Tilburg on May 20, 1986 and its Reexamination Patent No. B1 4,589,876, Certificate of Reexamination issued Apr. 27, 1993; U.S. Pat. No. 4,285,343, entitled "Sanitary Napkin", which issued to McNair on Aug. 25, 1981; U.S. Pat. No. 3,397,697, entitled "Disposable Sanitary Shield For Undergarments", which issued to Rickard on Aug. 20, 1968; and, U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, some women find applying sanitary napkins having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. As a result, some women still prefer a sanitary napkin without flaps. In addition, some women who generally prefer a sanitary napkin with flaps, occasionally (such as during periods of light flow) prefer a sanitary napkin without flaps. Therefore, there is a need for a sanitary napkin which provides an alternative to sanitary napkins having conventional side flaps while still providing the protection of side flaps.

Several variations of sanitary napkins having conventional flaps that attempt to solve some, but not all of these problems are disclosed in the patent literature. For example, U.S. Pat. No. 4,911,701 issued to Mavinkurve discloses a sanitary napkin having elastic strands for providing a greater convex shape to the body-facing portion of the central absorbent and for enabling adhesive-free placement of the flaps of a winged napkin embodiment into a pair of panties. The sanitary napkin described in the Mavinkurve patent, however, still appears to require the user to manipulate the flaps (by first flipping the flaps upward and then placing the flaps in her panties and flipping the flaps back down) since the flaps appear to be pre-disposed to be in a downward folded condition. The Mavinkurve patent also requires that individual elastic strands be attached in a contracted condition to the central absorbent portion of the napkin and/or to its wings or flaps. The napkins described in the Mavinkurve patent can, therefore, be difficult and expensive to manufacture. U.S. Pat. No. 4,940,462 issued to Salerno discloses a sanitary napkin with longitudinally expandable flaps. The flaps are designed to fold over the exterior of the wearer's panty and then to expand to conform with the contour of the panties. The sanitary napkin described in the Salerno patent, however, appears to require conventional adhesive fasteners to retain the flaps in place on the underside of the wearer's panties.

PCT Publication No. WO 95/03025, entitled "Absorbent Articles Having Undergarment Covering Components With Zones of Extensibility", published in the name of Weinberger, et al. on Feb. 2, 1995 discloses sanitary napkins that are believed to solve many of the aforementioned problems. However, there still remains a need for improving the performance of these sanitary napkins, especially to ensure that the undergarment covering components stay folded around the edges of the wearer's panties.

Thus, a need exists for an absorbent article, such as a sanitary napkin, that is provided with an alternative to conventional flaps. In particular, a need exists for a sanitary napkin having an alternative to conventional flaps which provides the protection from soiling of conventional flaps and which can conveniently and efficiently solve the problems caused when attempting to attach conventional flaps to the underside of the wearer's panties.

It is, therefore, an object of the present invention to provide an absorbent article, such as a sanitary napkin, that is able to provide coverage to the wearer's panties to reduce side soiling (i.e., staining of the edges of the panty crotch) without the use of conventional flaps.

It is another object of the present invention to provide an absorbent article, such as a sanitary napkin, that automatically folds at least partially around the sides of the wearer's panties by the simple action of the wearer pulling up her panties.

It is still another object of the present invention to provide an absorbent article, such as a sanitary napkin, that is able to fold around the sides of the wearer's panties and stay without providing flaps that have conventional panty fasteners thereon, and without attaching separate elastic strands to the sanitary napkin.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has a pair of undergarment covering components (or "side wrapping elements") that are provided with mechanical fasteners. In preferred embodiments, the present invention comprises a sanitary napkin having side wrapping elements that provide coverage to the wearer's panties to reduce side soiling (i.e., staining of the edges of the panty crotch) without the use of conventional flaps.

The sanitary napkin generally comprises a main body portion comprising a liquid pervious topsheet, a liquid impervious backsheet joined to the topsheet, and an absorbent core positioned between the topsheet and the backsheet. The side wrapping elements comprise a pair of flexible elements that extend beyond the crotch edge portions of the wearer's undergarment. The side wrapping elements are preferably joined to the garment-facing side of the main body portion inboard of the longitudinal side edges of the main body portion. The side wrapping elements are preferably each provided with at least one zone of extensibility, preferably two spaced apart zones of extensibility. The zones of extensibility are regions of the side wrapping elements that have a greater range of extension than the adjacent regions of the side wrapping elements. The side wrapping elements preferably comprise at least one zone of extensibility on each side of the transverse centerline of the side wrapping elements and a stiffer, less extensible intermediate region along the transverse centerline of the side wrapping elements.

The side wrapping elements have improved resistance to bending, crumpling, and other types of transverse deformation than a similar side wrapping element would have if it were made of the same material and was provided with extensibility along its full length. The stiffer, less extensible intermediate region located along the transverse centerline of the side wrapping elements provides the side wrapping elements with the improved resistance to bending and crumpling. The improved resistance to bending and crumpling ensures that the side wrapping elements will fold over the elasticated sides of the wearer's panties, and will not crumple when the wearer's thighs apply compressive forces on the distal edges of the side wrapping elements. The fact that the side wrapping elements have crumpling resistance and zones of extensibility allows the side wrapping elements to automatically fold around the crotch edge portions of the wearer's undergarment toward the underside of the undergarment and to remain so folded over the crotch edge when the absorbent article is placed in an undergarment and the undergarment is pulled up adjacent the wearer's body. The zones of extensibility and stiffer intermediate region, thus, provide a mechanism for controlling the manner and location of folding of the side wrapping elements.

The side wrapping elements preferably stay in place well enough to cover the side edges of the wearer's panties without affixing them underneath the wearer's panties. However, the side wrapping elements of the preferred embodiments described herein are preferably provided with a skin-friendly mechanical fastening material for additional security. The mechanical fastening material preferably affixes the side wrapping elements to the elasticated crotch edge portions of the wearer's panties (that is, the portions containing the panty elastics) so that the side wrapping elements can move with the panty elastics during wear. The fastener may also, but need not, affix a portion of the side wrapping elements to the underside of the wearer's panties. Preferably, the mechanical fastening material comprises a surface with an array of prongs in the form of a plurality of small filamentous (or hair-like) projections extending therefrom. The hair-like projections may be of any suitable shape. The hair-like projections may, but need not have a hook shape like conventional VELCRO hook fastening material. The hair-like projections are preferably able to automatically penetrate the material comprising the wearer's panties when the sanitary napkin is placed into the wearer's panties without any action on the part of the wearer. The hair-like projections prevent the side wrapping elements from bunching inward and unfolding from their folded configuration around the edge of the wearer's panties in the crotch edge portion when the elastics in the edges of the wearer's panties move and twist. The side wrapping elements are, thus, able to provide improved coverage of the side edges of the wearer's panties.

The sanitary napkin of the present invention provides an alternative to sanitary napkins having conventional side flaps for several reasons. The side wrapping elements do not extend far enough outward beyond the side edges of the wearer's panties to cause any inconvenience to the wearer. The side wrapping elements also require no action on the part of the wearer to fold the side wrapping elements under her panties or for the wearer to fasten the side wrapping elements to her panties.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
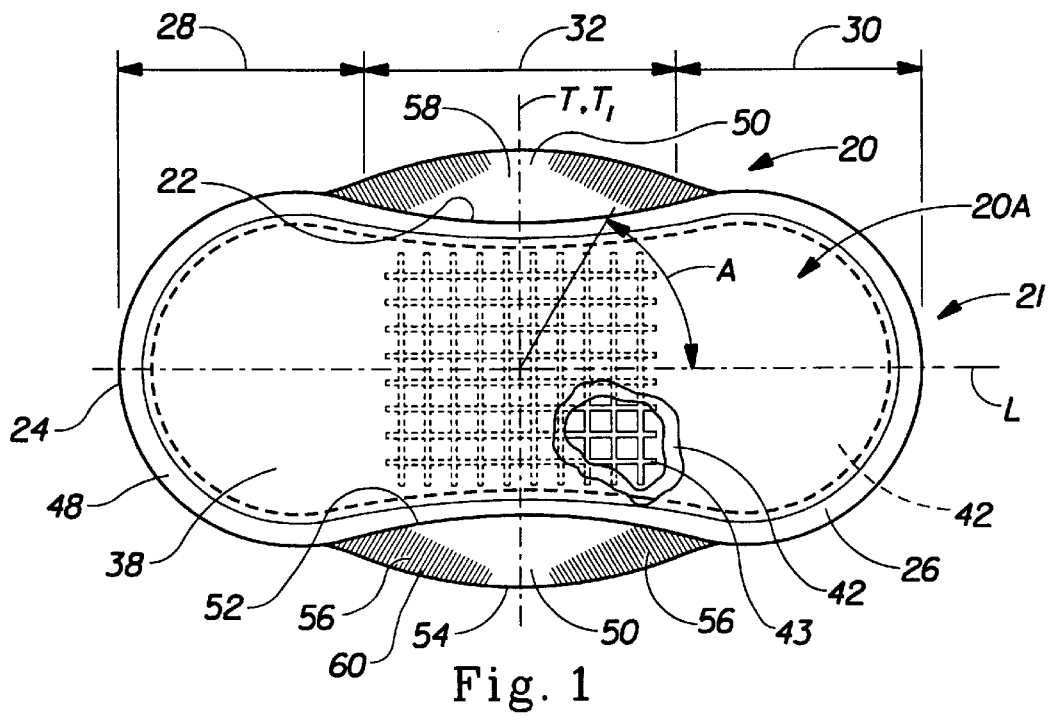
FIG. 1 is a top plan view of one embodiment of the sanitary napkin of the present invention.
Figure 2:
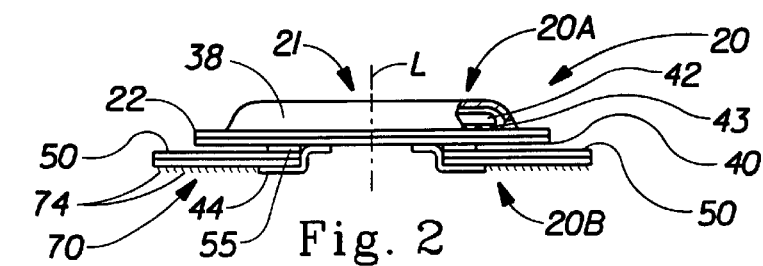
FIG. 2 is an end view of the sanitary napkin shown in FIG. 1 shown with a portion of the topsheet cut away to show the absorbent core and optional underlying scrim.
Figure 3:
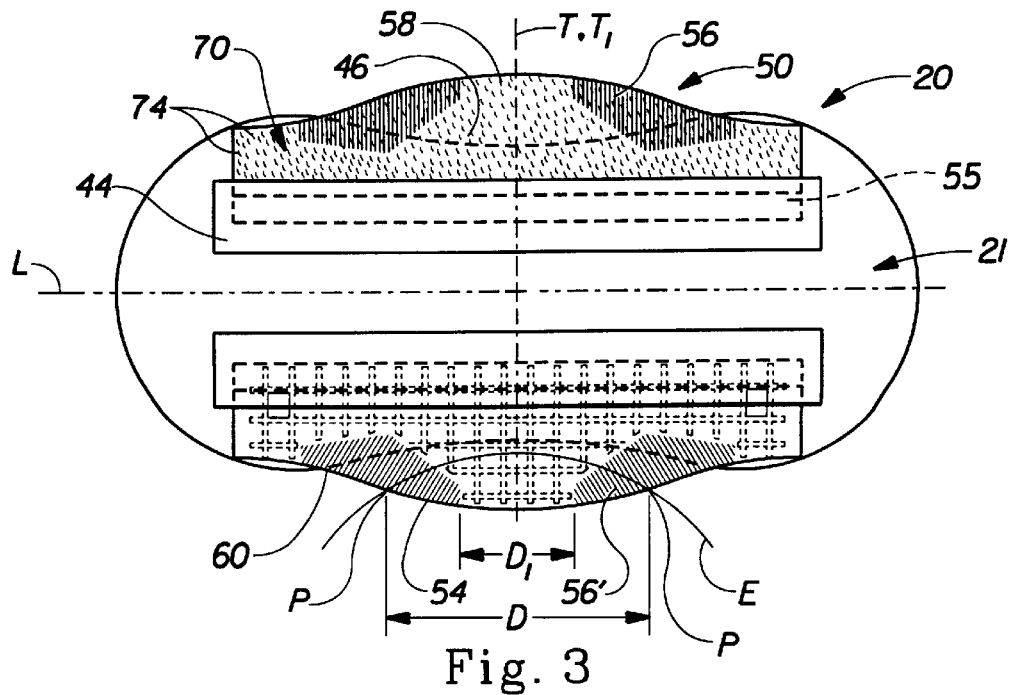
FIG. 3 is a slightly modified bottom plan view of the sanitary napkin shown in FIG. 1 in which the orientation of the ridges in the zones of extensibility in one of the side wrapping elements differs from that shown in FIG. 1, and the mechanical fasteners are removed from one of the side wrapping elements so an optional scrim in the side wrapping element may be seen more clearly.

The present invention relates to absorbent articles, such as sanitary napkins, panty liners, and incontinence pads. More particularly, the present invention relates to absorbent articles that have a main body portion and a pair of side wrapping elements that are provided with improved mechanical fasteners. Preferably, the side wrapping elements automatically fold around or wrap the sides of the wearer's undergarments when the wearer places the absorbent article in their undergarments and pulls their undergarments up. FIGS. 1–3 show one preferred embodiment of a disposable absorbent article of the present invention, sanitary napkin 20.

The sanitary napkin 20 (and the main body portion 21 thereof) has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 3) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral", used herein, are interchangeable, and refer to a line, axis or direction which lies within the plane of the sanitary napkin 20 that is generally perpendicular to the longitudinal direction.

FIG. 1 shows that the main body portion 21 of the sanitary napkin 20 comprises the portion of the sanitary napkin without the side wrapping elements. The main body portion 21 has two spaced apart longitudinal edges 22, two spaced apart transverse or end edges (or "ends") 24, which together form the periphery 26 of the main body portion. The main body portion also has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the main body portion. A detailed description of the characteristics of a central region and the two end regions for a sanitary napkin is contained in U.S. Pat. No. 4,690,680 issued to Higgins on Sep. 1, 1987.

The main body portion 21 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in FIGS. 1–3 of the drawings is intended to be an example of a sanitary napkin of intermediate thickness. The main body portion of the sanitary napkin 20 shown may also be relatively flexible, so that it is comfortable for the wearer. It should be understood that the sanitary napkin shown is merely one preferred embodiment, and that the present invention is not limited to absorbent articles of the type or having the specific configurations shown in the drawings.

FIG. 2 shows the individual components of the main body portion 21 of the sanitary napkin 20 of the present invention. The main body portion 21 of the sanitary napkin generally comprises at least three primary components. These include a liquid pervious topsheet 38, a liquid impervious backsheet 40, and an absorbent core 42 positioned between the topsheet 38 and the backsheet 40. In the embodiment shown in the first three figures, the main body portion 21 preferably comprises an optional scrim 43 positioned between the absorbent core 42 and the backsheet 40. The topsheet, the backsheet, and the absorbent core may be comprise any suitable components known in the art for such purposes.

In the embodiment shown in FIG. 2, the topsheet 38 comprises a three dimensional apertured formed film. The preferred apertured formed film topsheet 38 is made in accordance with U.S. Pat. No. 4,342,314 issued to Radel, et al. and U.S. Pat. No. 4,463,045 issued to Ahr, et al., and marketed on sanitary napkins by The Procter & Gamble Company under the name DRI-WEAVE. The liquid impervious backsheet 40 is preferably a polyethylene film of a type currently used on sanitary napkins marketed by The Procter & Gamble Company and described in greater detail in the following patents. The absorbent core 42 is preferably comprised of airfelt. An example of a suitable scrim 43 is a Conwed plastic scrim Lot #XN-4077 obtained from Conwed Plastics of Sussex, N.J. The sanitary napkin 20 may be assembled in a variety of configurations known in the art (including so called "sandwich" products and "tube" products).

Several preferred sanitary napkin configurations that can be provided with side wrapping elements having the improved mechanical fasteners used in the present invention are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. No. 4,950,264, "Thin, Flexible Sanitary Napkin" issued to Osborn on Aug. 21, 1990; U.S. Pat. No. 5,308,346, "Elasticized Sanitary Napkin" issued to Sneller, et al. on May 3, 1994; U.S. patent application Ser. No. 08/096,121 entitled "Absorbent Articles Having Panty Covering Components That Naturally Wrap the Sides of Panties" filed Jul. 22, 1993, in the name of Lavash, et al. (PCT Publication No. WO 94/02096, published Feb. 3, 1994); and U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. (PCT Publication No. WO 95/07675, published Mar. 23, 1995): and U.S. patent application Ser. No. 08/277,733 entitled "Absorbent Articles Having Undergarment Covering Components With Zones of Extensibility" filed Jul. 20, 1994 in the name of Weinberger, et al. (Publication No. WO 95/03025, published Feb. 2, 1995). The main body portion 21 of the sanitary napkin may also be comprised of one or more extensible components such as those sanitary napkins, and the like described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993).

FIGS. 1–3 show one preferred embodiment of the sanitary napkin 20 according to the present invention which is assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to thereby form portions of the periphery 26. The topsheet 38 is joined to the backsheet 40. The topsheet 38 and backsheet 40 can be joined in any suitable manner known in the art for this purpose. Preferably, the topsheet 38 and backsheet 40 are sealed at least partially around the periphery of the main body portion 21 by a peripheral crimp seal 48 where the topsheet 38 and backsheet 40 are densified by the application of pressure or heat and pressure.

The sanitary napkin 20 shown in FIGS. 1–3 also comprises pair of side wrapping elements 50 that extend laterally outward beyond the longitudinal side edges 22 of the main body portion 21 from their proximal edges 52 to their distal edges 54. The side wrapping elements 50 can be of any suitable size and shape. Preferably, however, the distal edges 54 of the side wrapping elements extend outward beyond the longitudinal side edges 22 of the main body portion 21, a distance of less than or equal to about one-half the width of the main body portion. The side wrapping elements 50 of may have the dimensions and characteristics set forth for the panty covering components in the aforementioned U.S. patent application Ser. Nos. 08/096,121, 08/124,180, and 08/277,733 filed in the names of Lavash, et al., Mansfield, et al., and Weinberger, et al., respectively, which are incorporated by reference herein.

The side wrapping elements 50 can, as shown in FIGS. 1–3, comprise two separate components that are joined to the garment-facing side 20B of the main body portion 21. The side wrapping elements 50 are preferably otherwise unattached to the garment-facing side of the main body portion 21 of the sanitary napkin 20 between the points of attachment and the longitudinal side edges 22 of the main body portion. The side wrapping elements 50 can be joined to the garment-facing side of the main body portion 21 by any suitable attachment mechanism. Suitable attachment mechanisms include, but are not limited to adhesives, and the like. In the embodiment shown, strips of adhesive 55 are used for this purpose.

The side wrapping elements 50 can, however, be joined to the main body portion 21 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Thus, the side wrapping elements 50 can be integral extensions of the topsheet 38 and backsheet 40 of the main body portion 21. In other embodiments, instead of comprising two separate components, the side wrapping elements 50 can comprise a single component (which may be referred to as a "panty covering component" or "undergarment covering component"). In still other embodiments, each side wrapping element 50 can comprise more than one component.

In the preferred embodiment shown in FIGS. 1–3, the side wrapping elements 50 each comprise a web of material or laminate having at least one, and preferably two zones of extensibility 56 therein. The zones of extensibility 56 can be primarily extensible in the longitudinal direction (that is, they are extensible more in the longitudinal direction than in the transverse direction). In other embodiments, the zones of extensibility 56 can be primarily extensible in the transverse direction, or in any direction between the longitudinal direction and the transverse direction. The side wrapping element 50 shown at the top of FIG. 3 has zones of extensibility that are primarily extensible in the longitudinal direction. The remaining zones of extensibility 56 in the embodiment shown in FIGS. 1–3 are extensible in a direction that is between the longitudinal direction and the transverse direction. The extensibility of all the zones of extensibility 56 on the side wrapping elements 50 can be in the same direction. Alternatively, one or more of the zones of extensibility 56 may be extensible in a different direction.

The zones of extensibility 56 are preferably capable of extending between about 20% and about 80%, more preferably between about 40% and about 60%, and most preferably about 50% under the forces associated with wearing the sanitary napkin in a pair of panties. Preferably, the zones of extensibility 56 are capable of such extension under forces of less than or equal to about 100–200 grams$_f$ per inch (about 40–80 g$_f$/cm), more preferably under forces of less than about 50 grams$_f$ per inch (about 20 g$_f$/cm). The zones of extensibility 56 are also preferably extensible without being elasticized or elasticated (that is, where separate elastic bands are stretched and attached to the side wrapping elements 50 in an extensible condition). Further, any inherent elasticity in the zones of extensibility 56 (that is, any tendency of the material comprising the zones of extensibility to return to its original dimension) is generally relatively low to non-existent. Preferably, the zones of extensibility 56 exhibit a return force of less than or equal to about 100 grams$_f$ when extended.

FIG. 3 shows the preferred locations for the zones of extensibility 56 and the manner in which the preferred amounts of extensibility in these locations are determined. The curved line, E, in FIG. 3 represents the location where the edges of a wearer's panty crotch might lie when the sanitary napkin 20 is placed in a pair of panties prior to the side wrapping elements 50 being folded around the edges of the panties. The panty edges E cross the distal edge 54 of the side wrapping element 50 at two points, designated P. The zones of extensibility 56 should be located where the panty edges E cross the distal edges 54 of the side wrapping elements 50. The distance, D, between these two points P varies depending on the size and style of panties. A representative distance D is equal to about 85 mm. FIG. 3 also shows portions 56' of the zones of extensibility that are disposed longitudinally inboard of the points P (that is, toward the transverse centerline T₁ of the side wrapping elements). In order to fit a wide variety of panty sizes and styles, it is preferred that each of the portions 56' of the zones of extensibility between points P is capable of extending greater than or equal to about 10–15 mm under the aforementioned forces and that the combined extensibility in these portions for each side wrapping element is greater than or equal to about 20–30 mm. The longitudinal distance between the points within zones of extensibility 56 that are on opposite sides of the transverse centerline of a side wrapping element 50 is preferably between about 20 mm and about 150 mm, and more preferably is between about 30–130 mm, and most preferably between about 30–100 mm.

The side wrapping elements 50, as shown in FIG. 3, preferably also have a trapezoidally-shaped intermediate region or zone 58 located between the zones of extensibility 56. The intermediate region 58 preferably has a distal edge portion that forms a portion of the distal edges 54 of the side wrapping elements. The length $D_1$ shown in FIG. 3 of the distal edge portion, is preferably at least about 20 mm, and more preferably about 30 mm. The intermediate region 58 is stiffer (that is, more resistant to bending) than the zones of extensibility 56. The intermediate region 58 is preferably also less extensible than the portions of the side wrapping elements that comprise the zones of extensibility 56. The intermediate region 58 provides the side wrapping elements 50 with greater resistance to bending and crumpling so that the side wrapping elements 50 will fold over the panty elastic, rather than crumple, when they are subject to compression by the wearer's thighs.

The configuration and location of the zones of extensibility 56 in the embodiment shown in FIGS. 1–3 is preferred for several reasons. The fact that the zones of extensibility 56 are spaced apart and separated by the stiffer intermediate region 58 provides improved resistance to undesirable crumpling while providing more control over the manner of folding around the edges of the wearer's panties. The side wrapping elements 50 will typically fold at those locations in the zones of extensibility 56 and the intermediate region 58 between the points where the panty edges cross the distal edges 54 of the side wrapping elements 50 that are situated along the panty elastics. The presence of the stiffer intermediate regions 58 makes the side wrapping elements sturdier and capable of more reliable folding than if the side wrapping elements 50 were made entirely extensible and/or were made of materials having the same stiffness over their entire area.

The stiffer intermediate region 58 also helps to maintain panty elastic coverage when the wearer pulls her panties down to check the sanitary napkin 20 for soiling, and then pulls her panties back up. The stiffer material ensures that the side wrapping elements 50 will go back into place in a downwardly folded configuration around the edges of the wearer's panties when the wearer pulls her panties back up.

The side wrapping elements 50 can be made from many of the materials known in the art for use in the construction of sanitary napkins. Suitable materials for the side wrapping elements 50 include, but are not limited to nonwoven materials, films, scrims, and laminates of such materials. Suitable nonwoven webs for use in the side wrapping elements 50 include a product known as Spunbond PE, which was obtained from Polybond, Incorporated of Waynesboro, Va., and a product known as COROLIND PE, which was obtained from Corovin GMBH of Germany. Suitable laminates comprise a nonwoven web such as one of those specified above which is laminated to another material, such as the three dimensional formed film known as DRI-WEAVE that is used as a topsheet on sanitary napkins manufactured by The Procter & Gamble Company, Cincinnati, Ohio, under U.S. Pat. No. 4,342,314 issued to Radel, et al. and U.S. Pat. No. 4,463,045 issued to Ahr, et al. Examples of suitable scrims are Conwed plastic scrim Lot Nos. ON-6200 and XN-6065 obtained from Conwed Plastics of Sussex, N.J. If a nonwoven laminate as described above is used in the side wrapping elements, the laminate is preferably oriented so that the nonwoven material faces upward so that it will be comfortable when placed against the wearer's body.

The side wrapping elements 50 in the embodiment shown in FIGS. 1–3 preferably comprise a laminate of three materials (only two of which are shown in FIG. 2 for simplicity of illustration). The three materials preferably comprise, from top (or body-facing side) to bottom (or garment-facing side): one of the nonwoven materials described in the preceding paragraph; the three-dimensional apertured formed film described above which is laminated to the nonwoven material; and a liquid impervious backing such as a polyethylene film backsheet which is laminated to the apertured formed film. The materials that comprise the side wrapping elements 50 can be laminated together by any suitable means known in the art. In addition, as will be described in greater detail below, the side wrapping elements 50 preferably have a skin-friendly mechanical fastening material 70 printed on the garment-facing side thereof.

The side wrapping elements 50 can be provided with zones of extensibility 56 in a non-limiting number of different manners. The side wrapping elements 50 may, for example, comprise a material that is substantially inextensible under the forces described above. The side wrapping elements 50 comprising such an inextensible material can have portions which are altered so that they are provided with extensible regions for the zones of extensibility 56. The extensible regions can be created in any suitable manner, including but not limited to mechanically straining, corrugating, "ring rolling", heating and deforming, subjecting portions of the side wrapping elements 50 to compression between mating plates, forming a network of distinct regions therein to provide portions of the side wrapping elements with the properties of a Structural Elastic-Like Film without added elastic materials (or the "SELFing" process described in allowed U.S. patent application Ser. No. 08/203,087 filed in the name of Chappell, et al. on Feb. 28, 1994 (PCT Publication No. WO 95/03765, published Feb. 9, 1995), and the like.

In other embodiments, the zones of extensibility 56 in the side wrapping elements can be provided by forming the side wrapping elements out of materials having different extensibilities. For example, the side wrapping elements 50 can be comprised of a laminate of an extensible material and a substantially inextensible material. In such an embodiment, the inextensible material can be provided in the configuration of the side wrapping elements. The inextensible material can have holes cut out where the zones of extensibility 56 are to be located. This inextensible material can then be laminated to the extensible material to form a side wrapping element with zones of extensibility 56 where the holes were cut out of the inextensible material.

The embodiment shown in FIGS. 1–3 has zones of extensibility 56 formed by ring rolling (or pre-corrugating) two regions of each of the side wrapping elements 50. Suitable methods for ring rolling are described in U.S. Pat. No. 4,107,364 issued to Sisson on Aug. 15, 1978, U.S. Pat.

No. 5,143,679 issued to Gerald M. Weber, et al. on Sep. 1, 1992, U.S. Pat. No. 5,156,793 issued to Kenneth B. Buell, et al. on Oct. 20, 1992, U.S. Pat. No. 5,167,897 issued to Gerald M. Weber, et al. on Dec. 1, 1992, and U.S. Pat. No. 5,366,782 issued to John J. Curro, et al. on Nov. 22, 1994.

The side wrapping elements 50 in most of the views of the embodiment shown in FIGS. 1–3 are provided with ring rolled corrugations having fold lines (or ridges and valleys) 60 that form an angled relative to the longitudinal centerline L. The fold lines 60 can form any angle, A, with the longitudinal centerline, between greater than 0° and less than or equal to 180°. The fold lines 60 in most of the views of the embodiment shown in FIGS. 1–3 form an angle of between about 40°–45° with the longitudinal centerline L. The side wrapping elements 50 in the upper portion of FIG. 3 show that in alternative embodiments, the ring rolling can be applied so that the fold lines 60 in the corrugations are oriented generally in the transverse direction to provide zones of extensibility 56 that are primarily extensible in the longitudinal direction.

The garment surface 20B of the sanitary napkin 20 may include, and preferably does include, fasteners for attaching the main body portion 21 of the sanitary napkin to the wearer's undergarment. FIGS. 2 and 3 show the central pad fastener 44 which is adapted to secure the main body portion 21 of the sanitary napkin to the crotch region of an undergarment. Any types of fasteners known in the art, such as adhesive fasteners and mechanical fasteners, can be used. Fasteners comprising adhesives have been found to work well for this purpose, with pressure-sensitive adhesives being preferred. As shown in FIG. 3, the central pad fastener 44 preferably comprises a pair of spaced apart longitudinally-oriented strips or zones of pressure sensitive adhesive. The zones of adhesive 44 are preferably centered about the longitudinal centerline L and are wide enough to overlap onto portions of the side wrapping elements 50. Before the sanitary napkin 20 is placed in use, if an adhesive fastener is used, the adhesive is typically covered with a removable cover strip or release liner in order to keep the adhesive from sticking to a surface other than the crotch portion of the panty prior to use. Suitable release liners are described in the U.S. Pat. No. 4,917,697. A particularly preferred release liner which also serves as an individual package of wrapping the sanitary napkin is described in U.S. Pat. No. 4,556,146 issued to Swanson, et al.

FIGS. 2 and 3 also show that portions of the garment-facing surface of the side wrapping elements 50 preferably comprise a skin-friendly mechanical fastening material 70. The mechanical fastening material 70 can be located on any suitable portion of the side wrapping elements 50 (or on any suitable portion of the main body portion 21). In the preferred embodiment shown in FIG. 3, the mechanical fastening material 70 is preferably located on the entire portion of the side wrapping elements 50, including the zones of extensibility 56, that lies laterally outboard of the zone of central pad adhesive fastener 44.

Figure 4:
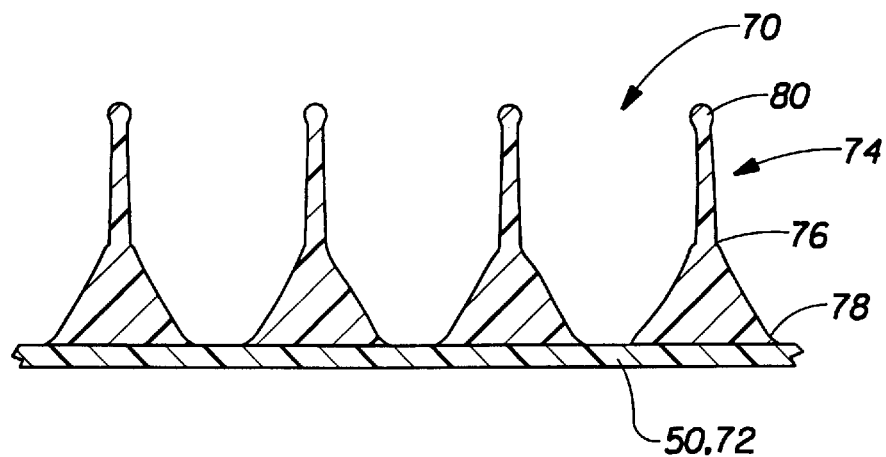
FIG. 4 is an enlarged side view of the mechanical fastening material with improved tactile properties that is used to maintain the side wrapping elements in place.

The mechanical fastening material 70 comprises a substrate or surface 72 with an array of prongs in the form of a plurality of small filamentous (or hair-like) projections 74 extending therefrom. The hair-like projections 74 may be of any suitable shape. FIG. 4 shows one preferred shape of the projections 74 in greater detail. The hair-like projections 74 may, but need not have a hook shape like conventional VELCRO hook fastening material. In the preferred embodiment shown in FIG. 4, the hair-like projections 74 preferably do not have a hook shape. The preferred hair-like projections 74 preferably have a straight shank 76 that tapers so that it generally decreases in diameter from the base 78 of the shank 76 toward the distal end of the shank. More specifically, the shank 76 decreases in diameter from the base 78 of the shank 76 toward the distal end of the shank until about the mid-point of the shank. The diameter of the shank 76 remains constant from about the mid-point of the shank to the distal end of the shank 76. The distal end of the shank 76 preferably has a small spherical engaging means 80 thereon. The hair-like projections 74 in the preferred embodiment shown in the drawings preferably extend approximately perpendicularly (that is, at an angle of about 90 degrees) from substrate. The angle that the hair-like projections 74 make with the garment-facing side of the side wrapping elements 50 may, however, vary slightly in the zones of extensibility 56 since the zones of extensibility will comprise a substrate that has corrugations formed therein.

The mechanical fastening material 70 can be made by printing or spraying a material to form small nubs on a surface or a substrate, such as a film. The nubs are then formed into the projections 74. The substrate 72 can be of any thickness or density. The substrate 72 can even include relatively rough or corrugated sections, such as the regions of the side wrapping elements that have zones of extensibility formed therein. The mechanical fastening material 70 described herein is particularly useful because it can be printed directly on substrates such as the backsheet and/or garment-facing side of the side wrapping elements. The mechanical fastening material can also be printed on a separate component that is joined to a portion of the sanitary napkin. In the preferred embodiment shown in the drawings, however, the substrate is the garment-facing side of the side wrapping elements.

The material that is used to form the nubs can be any suitable material that can be printed or sprayed on the substrate and formed into the projections described herein. Suitable materials include, but are not limited to thermal plastics and hot melt resins. The material used to form the projections 74 can be applied by any suitable printing or spray method (e.g., spiral, mist, line spraying, or gravure, rotary screen, or flexographic printing). Methods suitable for forming the projections 74 of the fastening material 70 are described in greater detail in U.S. Pat. No. 5,392,498 issued to Goulait, et al. on Feb. 28, 1995, which is hereby incorporated by reference herein. The projections 74 can have any suitable cross-sectional shape, including but not limited to oval, round, diamond, and pyramidal shapes. The print or spray pattern can be applied in any suitable pattern that produces dots, circles, lines, dimples, and the like, or it can comprise a combination of patterns. The material can be printed in regular or random patterns. The projections 74 formed thereby preferably extend outward about 0.05 mm to about 3 mm from the surface of the substrate 72.

In the preferred embodiment described above, the substrate 72 is a polyethylene film backsheet material and the printing resin is polyester. Two suitable polyester resins that can be used for this purpose are a resin known as A-3 obtained from Eastman Chemical Products, Inc. of Kingsport, Tenn. and a resin known as CA-X105 obtained from Century International Adhesives and Coatings Corporation of Columbus, Ohio. The latter polyester resin has a tackifier therein to provide the mechanical fastening material with higher adhesive tack. This aids the mechanical fastening material 70 in adhering to the wearer's panties. In this preferred embodiment, the mechanical fastening material 70 is printed on the zones of extensibility 56 by a rotary screen printing process. The printing can take place at any suitable stage in the manufacture of the sanitary napkin. Preferably, the mechanical fastening material 70 is printed on the side wrapping elements 50 before they have the zones of extensibility 56 formed therein by ring rolling the side wrapping elements 50. However, it is also possible that the mechanical fastening material 70 could be printed after the ring rolled regions are formed on the side wrapping elements 50. In such a case, the printing of the mechanical fastening material 70 could either take place when the zones of extensibility 56 are in an extended condition, or when they are in an unextended condition.

The polyester resin can be printed so that the hair-like projections 74 are distributed in any suitable density. Preferably, the projections 74 are distributed in the densities described in U.S. Pat. No. 5,392,498 issued to Goulait, et al. referred to above. More preferably, the hair-like projections 74 are distributed in densities that are at the higher end of the range described in the Goulait, et al. patent. For example, in preferred embodiments, the hair-like projections 74 are preferably distributed so that there are about 60 to about 100 rows of projections in both the machine and cross-machine directions per square inch (or about 3,600 to about 10,000 projections per square inch).

The mechanical fastening material 70 differs in several respects from conventional mechanical fastening material, such as VELCRO hook material and other fasteners commonly used on absorbent articles, such as adhesive fasteners. The mechanical fastening material 70 does not require a mating loop fastening component like VELCRO hook material. The mechanical fastening material can, instead, directly engage the fabric of the wearer's panties. The mechanical fastening material 70 used on the absorbent article of the present invention further differs from conventional mechanical fasteners due to the fact that is has projections that are substantially smaller than conventional VELCRO hooks. The projections are virtually unnoticeable to the wearer's eye. The mechanical fastening material 70 used in the present invention has improved tactile properties due to the small size and close spacing of the projections 74. As a result of the small size and close spacing of the projections 74, the wearer's skin tends to only feel the tips of the projections so that the mechanical fastening material tends to have a velvet-like feel.

The mechanical fastening material described herein is smoother, softer, and more flexible than conventional VELCRO fastening material. The increased flexibility allows the side wrapping elements 50 to fold more easily to conform to the wearer's panties. The mechanical fastening material, therefore, is less offensive (scratchy) than conventional VELCRO fastening material. The mechanical fastening material 70, since it can be printed directly on a substrate, can also utilize a greater variety of substrates (and is especially preferred for use with more flexible substrates). The mechanical fastening material 70 can, in some embodiments, also maintain the side wrapping elements 50 in place by friction and/or by adhesive attachment.

However, even when the mechanical fastening material 70 is provided with an adhesive-like tack, there is generally no need to apply separate release papers to cover the fastening material 70 on the side wrapping elements 50. Thus, the usual inconvenience of handling and disposing of such release papers is eliminated. In addition, the use of the mechanical fastening material avoids certain undesirable tendencies associated with the wearing of sanitary napkins having adhesive fasteners on side wrapping elements. For example, the mechanical fastening material eliminates the tendency of the adhesive on the side wrapping element to stick to itself and/or to the wearer's body. This is potentially a problem when the sanitary napkin is first placed in use. It is also potentially a problem during wear if the adhesive fastener should come unfastened to the wearer's panties, such as when the wearer pulls down her panties to check the sanitary napkin and during vigorous motions by the wearer.

Figure 6:
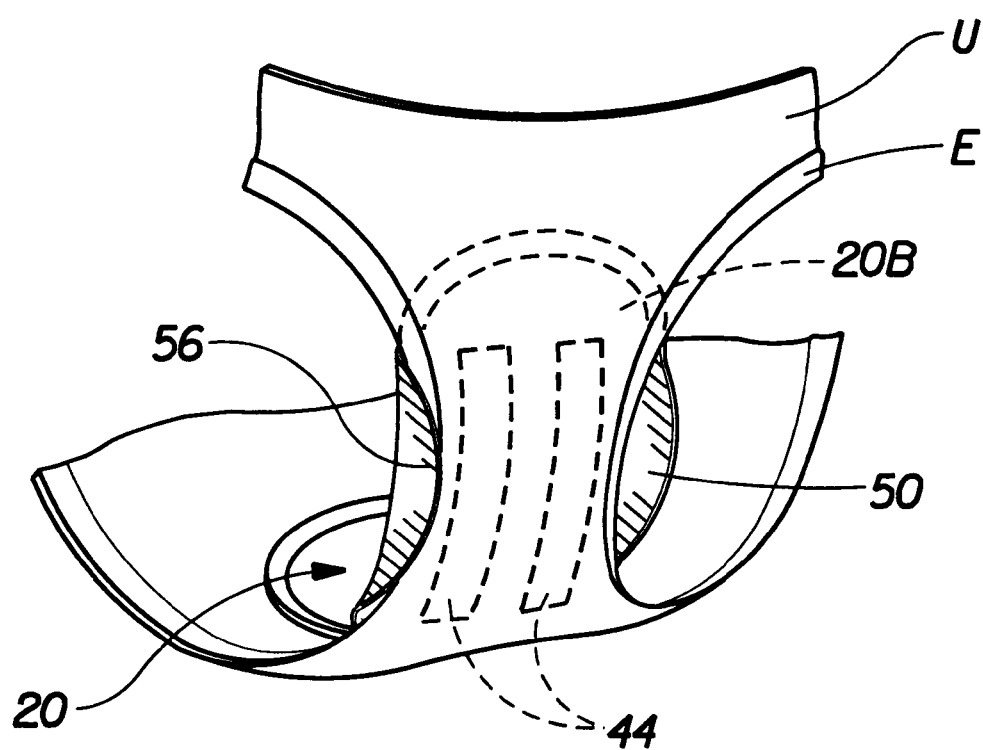
FIG. 6 is a perspective view of a portion of a panty showing one way in which the sanitary napkin of the present invention might fit in place with the side wrapping elements folded around the elasticized side edges of the wearer's panties.

The sanitary napkin 20 of the present invention is used by removing any release liner and thereafter placing the sanitary napkin 20 in a panty as shown in FIG. 6 so that the adhesive (or other fastener) 44 contacts the panty and maintains the sanitary napkin in position within the panty during use. The side wrapping elements 50 automatically fold along the sides of the wearer's panties by the simple action of the wearer pulling up her panties. The side wrapping elements 50 can assume an in-use position, one non-limiting example of which is shown in FIG. 6.

The operation of the side wrapping elements 50 is distinguishable in several aspects from that of conventional side flaps. First, placing a sanitary napkin having conventional flaps in a pair of panties and pulling up the panties will not consistently provide the automatic sustained wraparound feature of the present invention. There are several reasons for this. Conventional flaps are not provided with resistance to bending and crumpling so that they will tend to crumple in use, particularly when the wearer's thighs exert compressive forces on the flaps. Conventional flaps are also not provided with zones of extensibility, so they will generally not wrap around and conform to the panties. In those cases where conventional flaps do wrap around the panties, since conventional flaps do not have zones of extensibility they will not consistently stay wrapped. Second, conventionally-sized flaps will have excess flap material that hangs down underneath the panties during wear. This material can move around excessively underneath the panties and be uncomfortable for the wearer. The side wrapping elements of the present invention, on the other hand, have a span that is ideally just wide enough to wrap around the elastic-containing edges of the panties, but no wider, avoiding the problems associated with excess flap material.

The hair-like projections 74 of the mechanical fastening material 70 are preferably able to penetrate the material comprising the wearer's panties automatically upon placing the sanitary napkin in the wearer's panties and pulling up the panties. The mechanical fastening material 70 serves to maintain the side wrapping elements 50 at least partially folded around the elasticated edges of the crotch portion of the wearer's undergarments, especially during vigorous motions by the wearer.

One of the main problems that the mechanical fastening material 70 solves is illustrated in FIGS. 7–11. This problem tends to occur through sustained wear of the sanitary napkin 20 and during vigorous motions by the wearer when there is either no fastener on the side wrapping elements 50 or when there is an adhesive fastener on the side wrapping elements 50. The problem referred to herein is often exaggerated when the wearer is wearing older, and more loose-fitting undergarments (e.g., panties). FIGS. 7–11 show a sequence of events that can occur when the side wrapping elements 50 are provided with the improved mechanical fastening material, and when the side wrapping elements 50 are not provided with the improved mechanical fastening material described herein.

Figure 7:
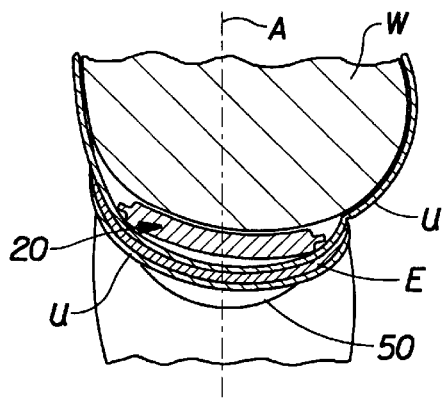
FIG. 7 is a simplified schematic side cross-sectional view of a wearer's body (taken along line B of FIG. 8) showing one way which a sanitary napkin with side wrapping elements might fit relative to the leg elastics of a relatively loose pair of panties.
Figure 8:
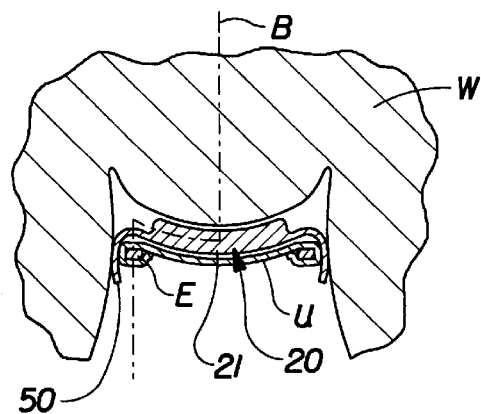
FIG. 8 is a simplified schematic cross-sectional view taken along line A of FIG. 7 showing the sanitary napkin having side wrapping elements positioned in the wearer's panties when the wearer's legs are about shoulder width apart.

FIG. 7 is a side cross-sectional view of a wearer's body, W, (taken along line B of FIG. 8) that shows one way which a sanitary napkin 20 with side wrapping elements 50 might fit relative to the leg elastics, E, of a relatively loose pair of panties. The wearer's panties are designated by reference letter U. FIG. 8 is a front cross-sectional view of the same subject matter shown in FIG. 7. FIG. 8 shows how the sanitary napkin 20 might fit in the wearer's panties when the wearer's legs are about shoulder width apart.

Figure 9:
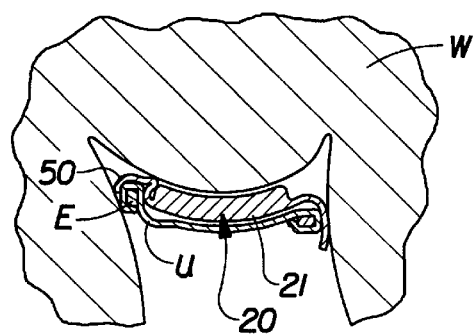
FIG. 9 is a schematic cross-sectional view similar to that of FIG. 8 showing how on one side the panty elastics tend to flip up from a relatively horizontal position to a more vertical position when the wearer makes certain body movements, and the way in which side wrapping element is pulled in as a result.

FIG. 9 is a cross-sectional view of the same portion of the wearer's body with the sanitary napkin in the wearer's panties. FIG. 9 shows how the panty elastics, E, on one side (the left side of the figure) tend to flip up from a relatively horizontal position to a more vertical position when the wearer makes certain body movements, such as when the wearer twists her body relative to her leg or when the wearer moves her foot to the side (e.g., side leg kick). FIG. 9 shows the way in which side wrapping element 50 on the left side of the sanitary napkin 20 is pulled in as a result.

Figure 10:
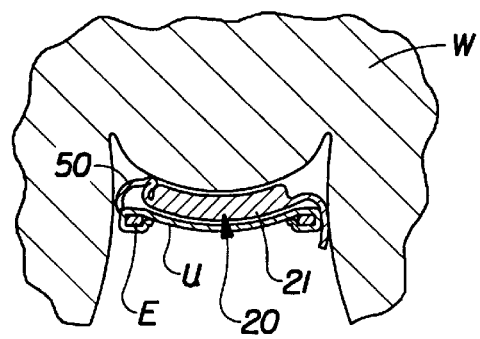
FIG. 10 is a schematic cross-sectional view similar to that of FIG. 8 showing how the side wrapping elements may leave the elasticized edge of the wearer's panties uncovered if the side wrapping elements are not provided with the improved mechanical fastening material described herein when the wearer's legs return to a position similar to that shown in FIG. 8 and the panty elastics flip back down.

FIG. 10 shows how the side wrapping element 50 may leave the elasticized edge of the wearer's panties uncovered if the side wrapping elements are not provided with the improved mechanical fastening material described herein. The circumstances shown in FIG. 10 may occur when the wearer's legs return to a position similar to that shown in FIG. 8 and the panty elastics flip back down to a horizontal position.

Figure 11:
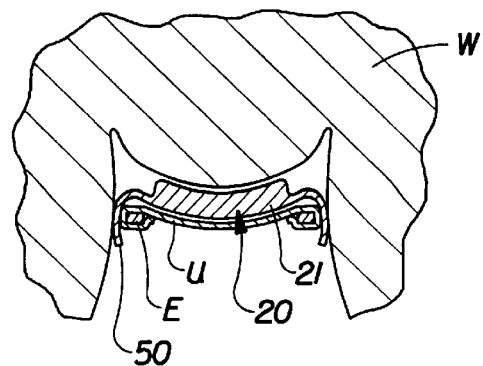
FIG. 11 is a schematic cross-sectional view similar to that of FIG. 8 showing how the side wrapping elements provided with the improved mechanical fasteners will move with the panty elastic when the panty elastics flip back down.

FIG. 11 shows how the side wrapping elements provided with a mechanical fastener will move with the panty elastic when the panty elastics flip back down to a horizontal position after the wearer's leg moves from the position described above relative to FIG. 9 to a position like that shown in FIG. 8. The hair-like projections are preferably able to penetrate the material comprising the wearer's panties to prevent the side wrapping elements from bunching inward and unfolding from their folded configuration around the edge of the wearer's panties (when the elastics in the edges of the wearer's panties move and twist). The side wrapping elements with the mechanical fastening material described herein, thus, provide improved coverage of the side edges of the wearer's panties. The following example demonstrates this.

EXAMPLE

A test is placed in which panelists engage in certain motions that might be encountered during their daily lives, such as when working in an office or while exercising. The test protocol requires that the panelists engage in the several activities in a specific order after the sanitary napkin is placed in their panties and loaded with a representative amount of liquid. These activities are: walking for five minutes; sitting in an office swivel chair for five minutes, and moving about in the chair in a manner that is typical while doing office work; and standing and kicking each leg to the side (that is, sideways leg kick) ten times starting with one leg, and finishing with the other leg. The percent loss in the area coverage provided by the side wrapping elements is measured after performing the test protocol.

The percent loss in area coverage is determined by measuring the length along the side of the crotch of the panties that is covered by the side wrapping elements. Measurements are taken before the panelist performs the test protocol when the sanitary napkin is initially placed in the wearer's panties and after the panelist performs the test protocol. The percent loss in area coverage is the difference in the amount of area coverage initially provided minus the area coverage provided after performing the test protocol divided by the initial area coverage. The percent loss in area coverage for a sanitary napkin having side wrapping elements that are not provided with the improved mechanical fastening material is about 65%. The percent loss in area coverage for a sanitary napkin of the present invention, on the other hand, is about 28%.

Figure 5:
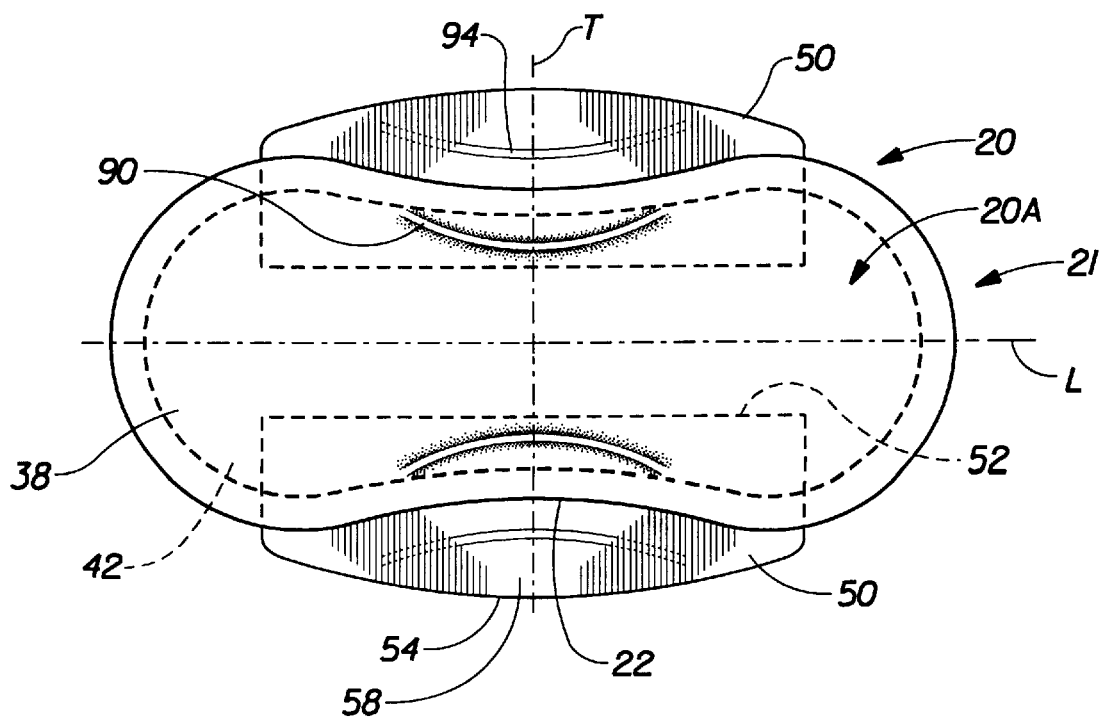
FIG. 5 is a top plan view of a sanitary napkin having side wrapping elements with an alternative configuration and optional score lines.

Numerous alternative embodiments of the present invention are possible. For example, the side wrapping elements are preferably mirror images of each other, and are symmetrical about the longitudinal centerline. However, it should be understood that the shape and location of the side wrapping elements described herein are those of a preferred embodiment, and other embodiments are also possible. For example, FIG. 5 shows another embodiment of a sanitary napkin 20 which can utilize the improved mechanical fastening material described herein. The embodiment shown in FIG. 5 has side wrapping elements 50 which have a different configuration from those of the embodiment shown in FIGS. 1–3. The side wrapping elements 50 are also provided with a region that has two concentric concave score lines 94 which are oriented side-by-side to provide the side wrapping elements with a distinctive hinge structure.

The present invention is also applicable to other types of absorbent articles worn in the crotch region of an undergarment such as pantiliners and incontinence articles. The terms "panty liner" or "pantiliner" refer to absorbent articles that are less bulky than sanitary napkins which are generally worn by women between their menstrual periods. Suitable absorbent articles in the form of pantiliners that can be provided with the side wrapping elements described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the side wrapping elements described herein are disclosed in U.S. Pat. No. 5,300,054 issued to Feist, et al. on Apr. 5, 1994 and U.S. Pat. No. 5,304,161 issued to Noel, et al. Apr. 19, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing in a wearer's undergarment that has a crotch region with a pair of side edges, said absorbent article having a longitudinal dimension extending in a longitudinal direction and a transverse dimension extending in a transverse direction, said absorbent article comprising:

a main body portion comprising an absorbent core, said main body portion having a body-facing side, a garment-facing side, and a pair of longitudinal side edges; and a pair of side wrapping elements for at least partially folding around the side edges of the wearer's undergarment, said side wrapping elements having a body-facing side and a garment-facing side, said side wrapping elements being joined to said main body portion and extending laterally outward beyond the longitudinal side edges of said main body portion a distance of less than or equal to about one-half the width of said main body portion, to distal edges, said side wrapping elements having a transverse centerline, wherein at least one of said side wrapping elements comprises at least one zone of extensibility and another region that is stiffer than said at least one zone of extensibility, said at least one zone of extensibility being extensible when folded around the side edges of an undergarment wherein said at least one zone of extensibility is capable of extending between about 20% and about 80% under forces of less than or equal to about 200 grams per inch, wherein at least a portion of the garment-facing side of said side wrapping elements comprises a skin-friendly mechanical fastening material for engaging at least a portion of the wearer's undergarment, said mechanical fastening material comprising an array of prongs, each of said prongs comprising a base joined to a substrate, an engaging means, and a shank comprising a proximal end joined to said base and a distal end joined to said engaging means.

2. The absorbent article of claim 1 wherein said mechanical fastening material is located on a portion of said side wrapping element that will engage the side edges of a wearer's undergarment when said side wrapping elements are at least partially folded around the side edges of a wearer's undergarment.

3. The absorbent article of claim 1 wherein at least one of said prongs of said mechanical fastening material has an included angle relative to said substrate of about 90 degrees.

4. The absorbent article of claim 3 wherein said engaging means on said at least one prong of said mechanical fastening material is spherical.

5. The absorbent article of claim 1 wherein said substrate comprises the garment-facing side of said side wrapping elements.

6. The absorbent article of claim 5 wherein said prongs comprise a resin that was printed directly onto said garment-facing side of said side wrapping elements.

7. The absorbent article of claim 1 wherein said mechanical fastening material comprises a tackifier.

8. The absorbent article of claim 1 wherein said array of prongs comprises from about 3,600 to about 10,000 prongs per square inch.

9. The absorbent article of claim 1 wherein said zones of extensibility are primarily extensible in the longitudinal direction.

10. The absorbent article of claim 1 wherein said zones of extensibility are primarily extensible in the transverse direction.

11. The absorbent article of claim 1 wherein said zones of extensibility are extensible in a direction between the longitudinal direction and the transverse direction.

* * * * *